United States Patent
Lipshaw et al.

(10) Patent No.: US 12,403,027 B2
(45) Date of Patent: *Sep. 2, 2025

(54) COMPRESSION GARMENT

(71) Applicant: MEDI USA, L.P., Whitsett, NC (US)

(72) Inventors: Moses Lipshaw, Whitsett, NC (US); Thomas Richardson, Whitsett, NC (US); Karen Lynch, Whitsett, NC (US); Kevin Larmer, Whitsett, NC (US)

(73) Assignee: MEDI USA, L.P., Whitsett, NC (US)

( * ) Notice: Subject to any disclaimer, the term of this patent is extended or adjusted under 35 U.S.C. 154(b) by 296 days.

This patent is subject to a terminal disclaimer.

(21) Appl. No.: 17/543,619

(22) Filed: Dec. 6, 2021

(65) Prior Publication Data
US 2022/0087848 A1    Mar. 24, 2022

Related U.S. Application Data

(63) Continuation of application No. 16/311,283, filed as application No. PCT/US2017/040269 on Jun. 30, 2017, now Pat. No. 11,395,752.

(60) Provisional application No. 62/356,978, filed on Jun. 30, 2016.

(51) Int. Cl.
| | |
|---|---|
| A61F 5/01 | (2006.01) |
| A41B 11/00 | (2006.01) |
| A61F 13/06 | (2006.01) |
| A61F 13/08 | (2006.01) |

(52) U.S. Cl.
CPC ............. *A61F 5/0111* (2013.01); *A41B 11/00* (2013.01); *A61F 13/064* (2013.01); *A61F 13/085* (2013.01); *A41B 2300/32* (2013.01)

(58) Field of Classification Search
CPC ...... A61F 5/0111; A61F 13/06; A61F 13/064; A61F 13/066; A61F 13/08; A61F 13/085; A41B 11/00; A41B 2300/32
See application file for complete search history.

(56) References Cited

U.S. PATENT DOCUMENTS

| | | |
|---|---|---|
| 5,897,518 A | 4/1999 | Shaw |
| 5,918,602 A | 7/1999 | Shaw et al. |
| 7,329,232 B2 | 2/2008 | Lipshaw et al. |
| 8,491,514 B2 | 7/2013 | Creighton et al. |
| 10,980,675 B2 | 4/2021 | Lipshaw et al. |
| 11,395,752 B2 * | 7/2022 | Lipshaw ................. A61F 5/01 |
| 2003/0171706 A1 | 9/2003 | Nelson |

(Continued)

FOREIGN PATENT DOCUMENTS

DE    19638683 A1    4/1998

*Primary Examiner* — Keri J Nelson
(74) *Attorney, Agent, or Firm* — Rimon PC (57) ABSTRACT

A compression garment for a limb is disclosed. The garment can include a body portion and a spine portion. Each of the body and spine portions can have a plurality of bands (e.g. bands for adjusting tension of the garment). The spine portion can be releasably attached onto the body portion such that the spine portion is positionable at different locations on the body portion to adjust a width of the garment. The bands of the body portion and/or of the spine portion can be trimmable and include a detachable fastener, whereby as a result the band can be caused to move to a plurality of different positions to adjust the garment to a plurality of different sized limbs (e.g. different sized feet).

21 Claims, 8 Drawing Sheets

(56) References Cited

U.S. PATENT DOCUMENTS

| | | |
|---|---|---|
| 2011/0125183 A1 | 5/2011 | Lipshaw et al. |
| 2013/0283500 A1 | 10/2013 | Lipshaw et al. |
| 2013/0319128 A1 | 12/2013 | Richardson et al. |
| 2015/0025424 A1 | 1/2015 | Richardson et al. |
| 2016/0058623 A1 | 3/2016 | Lipshaw et al. |

\* cited by examiner

COMPRESSION GARMENT

FIELD

The present application is a Continuation application of U.S. application Ser. No. 16/311,283, filed Dec. 19, 2018, which is a United States national stage entry of International Patent Application No. PCT/US2017/040269 filed Jun. 30, 2017, which claims priority to U.S. Provisional Patent Application No. 62/356,978 filed Jun. 30, 2016. Each of these applications is incorporated by reference in its entirety.

FIELD

Compression garments for the treatment of circulatory disorders such as Lymphedema.

BACKGROUND

Lymphedema is swelling that occurs when excessive protein-rich lymph fluid accumulates in the interstitial tissue. This lymph fluid may contain plasma proteins, extravascular blood cells, excess water, and parenchymal products. Lymphedema is one of the most poorly understood, relatively underestimated, and least researched complications of common diseases like cancer, and thus the prevalence of lymphedema within the general population is largely unknown. Nevertheless, for those who are diagnosed with lymphedema, the standard of care consists of meticulous skin care, manual lymphatic drainage, exercise therapy, inelastic compression bandaging and, eventually, compression garments. In regard to edema in the lower extremity, specifically the ankle-foot region, treatment can be additionally challenging due to the joint transition and increased likelihood of edema accumulation creating folds, lobules, and other abnormalities in the foot area. Individuals with edema often have limited range of motion which makes the distal ankle-foot area difficult to access for self-treatment.

The frequency and duration of care is dependent on individual subject's therapeutic need and may range from 2 to 3 visits per week for 6 or more weeks depending on the severity of lymphedema and any other associated impairment.

The use of compression bandaging, although proven effective in reducing edema, has its drawbacks. The application of inelastic compression bandages is time consuming and requires a skilled clinician. Furthermore, because subjects are not able to effectively bandage themselves, this treatment strategy does not promote self-care, does not provide sustained therapeutic levels of compression, and requires the subject to frequently return for follow up visits. Lastly, wearing bandages negatively impacts the subject's quality of life with regard to comfort and hygiene which can reduce compliance.

Many bandage alternative wrap type garments exist on the market. These garments are primarily used after the intensive phase treatment of lymphedema to maintain the patient's limb size. Most of the wrap garments lack the ability to adapt to changes in limb size and are cost prohibitive to be used as a short term bandage replacement in the intensive phase. For those garments that are available the sizing adjustments can be complex and time consuming for practical use. The embodiments of the present disclosure address these and other related needs in the art.

SUMMARY

In some embodiments, a compression garment for a limb is disclosed. The garment can include a body portion and a spine portion. Each of the body and spine portions can have a plurality of bands (e.g. bands for adjusting tension of the garment). The spine portion can be releasably attached onto the body portion such that the spine portion is positionable at different locations and angles on the body portion to adjust a width or contour of the garment. The bands of the body portion and/or of the spine portion can be trimmable and include a detachable fastener, whereby as a result the band can be caused to move to a plurality of different positions to adjust the garment to a plurality of different sized limbs (e.g. different sized feet and/or corresponding circumferences). The bands may extend at different angles from the body and/or spine portions. In certain embodiments, the limb can therefore be a foot.

In some embodiments, the spine portion can include an aperture in at least one of the bands of the spine portion. At least one of the bands of the body portion can extend from a lower edge of the body portion and be caused to pass through and interlocks with the aperture. In some embodiments, passing through and interlocking the band of the body portion with the spine portion can form a heel cup or contoured surface operable to conform to and support a heel. The heel cup can also be operable to adjust a distal end of the garment to a plurality of different foot lengths and/or align an arch portion of the garment over the foot In some embodiments, the spine portion can include an inner edge that attaches onto the body portion. The inner edge can include one or more detachable fasteners. In some embodiments, the spine portion and/or the body portion can include indicia corresponding to a dimension of the limb (e.g. dimensions of the foot). For example, the dimension can correspond to a plurality of foot, arch, and/or ankle circumferences such that the spine portion can be trimmable along the indicia to conform to a specific circumference of the user. Advantageously, as the user's respective circumference can change shape during treatment, the spine portion and/or body portion can be conformed to the user's ankle without the need to replace with a separate garment or separate spine portion. In other embodiments, the dimension can correspond to a plurality of feet widths, feet circumferences, foot lengths, shoe sizes, so that the spine portion and/or body portion is trimmable along the indicia to conform to the respective dimension of the user.

In some embodiments, the distal ends of one or more of the bands includes a detachable fastener tab. The one or more of the bands can be trimmable with the fastener tab being detachably positioned on the distal end.

In some embodiments, the spine portion can include one or more fastener tabs.

In some embodiments, the spine portion can include an inner edge that attaches onto the body portion. At least one of the bands of the spine portion can be an ankle band that extends away from an outer edge opposite the inner edge. The at least one band of the spine portion for the ankle can be longer and thinner than other of the bands of the spine portion.

In some embodiments, the body portion can include a central region with an inner edge, an outer edge opposite the inner edge, an upper edge, and a lower edge. In this respect, the plurality of bands of the body portion can include at least one band extended from the outer edge and at least one band extended from the lower edge.

In some embodiments, the spine portion can also include a central region with an inner edge, an outer edge opposite the inner edge, an upper edge, and a lower edge. The plurality of bands of the spine portion can include at least one band extended from the outer edge and at least one band extended from the lower edge. The plurality of bands of the spine portion can include at least one band extended between the bands that are extended from the upper and lower edges. The plurality of bands of the spine portion can include at least one band longer than the other bands and extended curved away from the outer edge substantially normal to the upper edge of the spine portion. A notch or indentation for prevention of gapping can also be disposed between the at least one band extended curved away from the outer edge and the other bands of the spine portion. The at least one band extended curved away can be configured to prevent a gap between the other bands of the body and spine portions when assembled about the limb (e.g. a foot).

In some embodiments, the at least one of the body portion, spine portion, and/or corresponding bands further comprises one or more compression portions. The one or more compression portions can be inelastic. The one or more compression portions can be an upraised portion selectively positioned and operable to apply pressure to an area of the user.

In some embodiments, the body portion and/or the spine portion includes a top edge, a bottom edge and a pair of opposite side edges. The body and/or spine portion can be trimmable between the edges permitting the body portion and/or spine portion to correspond to any shape of the limb.

In some embodiments, the bands of the body portion and/or the spine portion are of a more elastic material and the corresponding body and/or spine portion is of an elastic or less stiff material. The stiffer material can be capable of folding and conforming to contours of the limb thereby rendering the garment less constricting. The body portion can include an inner surface and an outer surface, the outer surface being stiffer than the inner surface.

In some embodiments, all of the bands are stiffer than the body and spine portions. In some embodiments, one or more of the bands of the body and/or spine portion are trimmable and comprise indicia for trimming. In some embodiments, the spine portion is angleable on the body portion at a plurality of orientations. In some embodiments, the body portion is elastic and the spine portion is inelastic. In some embodiments, the spine portion is elastic and the body is inelastic. In some embodiments, the tension bands are substantially elastic and the body and spine portions are inelastic or include one or more inelastic portions.

In some embodiments, a compression and/or tension level measuring system can be provided in the garment for indicating an actual compression level delivered to the limb by the garment, wherein the limb is a foot. The system can be configured to measure indicia the garment when the garment is donned by the foot with a card comprising a scale for measuring a separation of at least one indicia to determine an actual compression level to the foot associated with the separation. At least one end of the at least one of the bands of the body portion and the spine portion can be releasably attachable to a plurality of locations and orientations so that the at least one band is adjustable between a plurality of compression levels according to the actual compression level measured by the system.

In some embodiments, the system can be disposed on the body portion and/or the spine portion and include a stretchable base layer and an upper layer attached at two spaced-apart locations on top of the stretchable base layer. A visual indicator of the actual compression level can be positioned with the upper or base layers and can be observable when the upper layer is pulled taut.

In other embodiments, method of fitting a compression garment to a foot is disclosed. The method can include selectively positioning a plurality of bands on a body portion of the garment; selectively positioning a plurality of bands on a spine portion of the garment; adjusting a width of the garment by selectively attaching an edge of the spine portion onto the body portion; selectively trimming the bands and/or the spine portion; attaching a detachable fastener onto one or more of the bands; wrapping the body and spine portions around part of the foot; and wrapping each of the bands around the body and spine portions and part of the foot to apply a therapeutic compression to the foot.

In other embodiments, the method can include selectively positioning an aperture in one of the bands of the spine portion, the aperture being between a proximal and a distal edge; and passing through and interlocking one of the bands of the body portion through the aperture. In some embodiments, the method can also include trimming, before the passing through and interlocking, the band of the spine portion with the aperture and/or the one of the bands of the body portion being passed through the aperture; and detachably positioning a fastener tab on a distal end of the band of the spine portion with the aperture and/or the one of the bands of the body portion being passed through the aperture. The trimming can be is along indicia corresponding to a dimension of the foot (e.g. a length of the foot).

In other embodiments, the method can include trimming a sizing section of the body portion by adjusting a location of the spine portion on the body portion; trimming excess material of the body portion; and adjusting a height of the bands that are interlocking.

In other embodiments, the method can include forming a heel cup by the passing through and interlocking one of the bands of the body portion through the aperture; and conforming, by the heel cup, the garment to a heel of the foot. The method can also include forming a heel cup by the passing through and interlocking one of the bands of the body portion through the aperture; adjusting, by the heel cup, a distal end of the garment to a plurality of different foot lengths; and aligning, by the heel cup, an arch portion of the garment over the foot.

In other embodiments, the method can include pulling bands of the body and spine portions in opposing directions around the foot. In other embodiments, the method can include comprising: trimming the bands of the body portion and/or the spine portion to a preferred size, by measuring a dimension of the foot at one or more locations, and trimming the respective band such that the respective band corresponds to the foot at each of the one or more locations.

In other embodiments, the method can include trimming the body portion and/or the spine portion to a preferred size, by: measuring a dimension of the foot at one or more locations, and trimming the body portion and/or the spine portion such that top and bottom edges of the body portion and/or the spine portion correspond to the foot at each of the one or more locations.

In other embodiments, the method can include extending at least one band of the body portion from the outer edge of the body portion and/or spine portion; and extending at least one band of the body portion from the lower edge of the body portion and/or spine portion. Each of the at least one bands can be substantially normal to the other. In some embodiments, the method can include extending another band of the spine portion between the bands extended from the upper and lower edges. In some embodiments, the method can include extending and curving upward substantially normally another band of the spine portion between the bands extended from the upper and lower edges. In some embodiments, the method can include positioning a detachable fastener on a distal end of the another band; wrapping the another band around an ankle of the foot; and detachably connecting the distal end of the another band onto the body or spine portions. In some embodiments, the method can include trimming a length of the another band, after the distal end being detachably connected on the body or spine portion; and then detachably connecting the distal end of the another band onto the body or spine portions.

In some embodiments, the method can include positioning a notch or indentation between another band and the other bands of the spine portion thereby preventing formation of a gapping in the garment. In some embodiments, the method can include juxtaposing the bands of the body and spine portion between one another when wrapped around the part of the foot.

In some embodiments, the method can include positioning indicia on the body portion, the spine portion, and/or one or more of the bands, the indicia corresponding to a dimension of the foot; and trimming the body portion, the spine portion, and/or one or more of the bands according to the indicia.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION

Unless defined otherwise, all terms of art, notations and other scientific terms or terminology used herein have the same meaning as is commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "subject" is not limited to a specific species. For example, the term "subject" may refer to a patient, and frequently a human patient. However, this term is not limited to humans and thus encompasses a variety of mammalian species.

As used herein, the term "elastic" as it pertains to compression garments can relate to garments and/or materials and/or portions of garments that can be stockings, wraps, or any portion thereof, both circular and flat knit, which can incorporate elastic fibers such as spandex or latex. It is this elastic fiber that enables the garment to provide compression and also to stretch in order to apply the garment to the limb. Because of the elastic nature of the garment in this respect, a consistent or static compression to the limb can be applied; when an individual changes position, such as moving from supine to standing, the limb circumference changes. This elastic nature stretches to accommodate the change in circumference and maintains a fairly consistent compression level regardless of position or movement. This is particularly beneficial when a patient experiences a reduction in limb size due to the removal of excess edema in the treated limb. However it also requires that the compression garment be removed when in a supine position because a consistent high compression level may result in pain in the limbs due to the decreased venous pressure.

As used herein, the term "non-elastic" or "inelastic" can be the opposite or substantially opposite of elastic materials and/or elastic compression. Garments, or constituent materials that are non-elastic, may not stretch, or may have limited stretch when a limb circumference changes (e.g. as the result of body movement). A non-limiting example of non-elastic material can be Velcro 3610 though other material or combination of materials can be included with less or more stretch and still qualify as non-elastic as that term is used herein. Other non-limiting examples of limited stretch material can be breathoprene, neoprene, and similar laminates and/or materials that are able to be utilized in inelastic compression designs.

As used herein, the term "substantially" or "substantial" is a meaningful modifier implying "approximate" rather than "perfect." For example, the term "substantially normal" is used because it will be appreciated that a reference edge or reference line of a particular portion of the garment may not be perfectly "normal."

Compression therapy is considered the mainstay of treatment for lymphedema which relies on the application of external force in order to increase the internal pressure of the affected limb. Almost any portion of the body can suffer from swelling. Additionally, following open heart surgery, compressive support is critical for managing pain and preventing strain on the surgery site. There are several approaches to resolve these and other problems of the art.

A first approach has included bandaging. This typically involves a therapist wrapping the patient's foot, and sometimes toes, in order to apply the desired level of compression. The bandages are then left in place for as long as possible. While effective, this approach requires a degree of skill and training that is not available to everyone. As a result, individuals who are unable to treat and bandage themselves are often required to leave bandages applied by trained professionals in place for extended periods of time. This often leads to hygiene concerns and is significantly inconvenient.

A second approach has included compression stockings. Compression stockings can also be used to apply therapeutic compression. They can be knit, sewn, made custom to the user's measurements, standard sized, and be composed from a variety of elastic and inelastic materials. While also effective, these stockings typically fall short when swelling reduction is needed and are primarily used for maintenance once swelling has been reduced. Due to the intended use of the products, they are tight fitting by nature which often translates into fit issues and can be challenging to don particularly for users with limited hand strength and dexterity (e.g. elderly individuals). Custom stockings made to the patient's measurements can help resolve some of the fit complications. However, even those have issues and can be prohibitively expensive.

A third approach has included ankle foot wraps. This approach typically involves a wrap for applying compression to the foot and ankle and includes a body portion paired with one or more bands or straps that are used to apply compression. Ankle foot wraps provide a reasonable alternative to bandaging as they enable the user to wrap their foot more easily without training or a special skill set. However, unlike bandages, there is less flexibility with sizing. A bandage can be used to fit almost any foot regardless of shape and size, while foot wraps are more size specific (e.g. limited to sizes such as small, medium, large and only one length) and designed for the natural contours of the foot.

Known foot wrap garments and stocking options also suffer from delay and reduced treatment time. For example, the patient needs to be measured prior to determining the product size, and then the patient is required to order or find a dealer location where they can purchase the product. This can take weeks which delays treatment and may waste one of the set number of therapy sessions allotted by the insurance companies.

In certain embodiments a garment for a foot of the present disclosure comprises a one-size-fits-all, easy-to-use, trimmable for customized fitting, for instantly adjustable compression that resolves these and other problems of the art. Specifically, the proposed solution may be a foot wrap that resolves issues related to sizing and fit. The foot wrap may have one or more body portions that can accommodate different foot circumferences, widths, and lengths as treatment progresses and changes the shape of the foot. The herein disclosed foot wrap is operable permit the user to target specific areas along the heel and ankle region.

Unlike other approaches, particularly the one shown in U.S. Pat. No. 8,376,977 by Farrow Innovations, LLC, trimming the body portion does not necessarily require indicia and effectively customizes how the wrap fits and where the interlocking bands target their compression. Trimming bands to accommodate the appropriate circumference does not require any measurements and can be done during the initial application process. In contrast to the '977 Patent, the herein disclosed solution offers the unique customization options mentioned herein. Additionally, when being used during the reduction phase of lymphedema treatment, the foot wrap can be continuously resized as foot and ankle swelling reduces.

Figure 1:
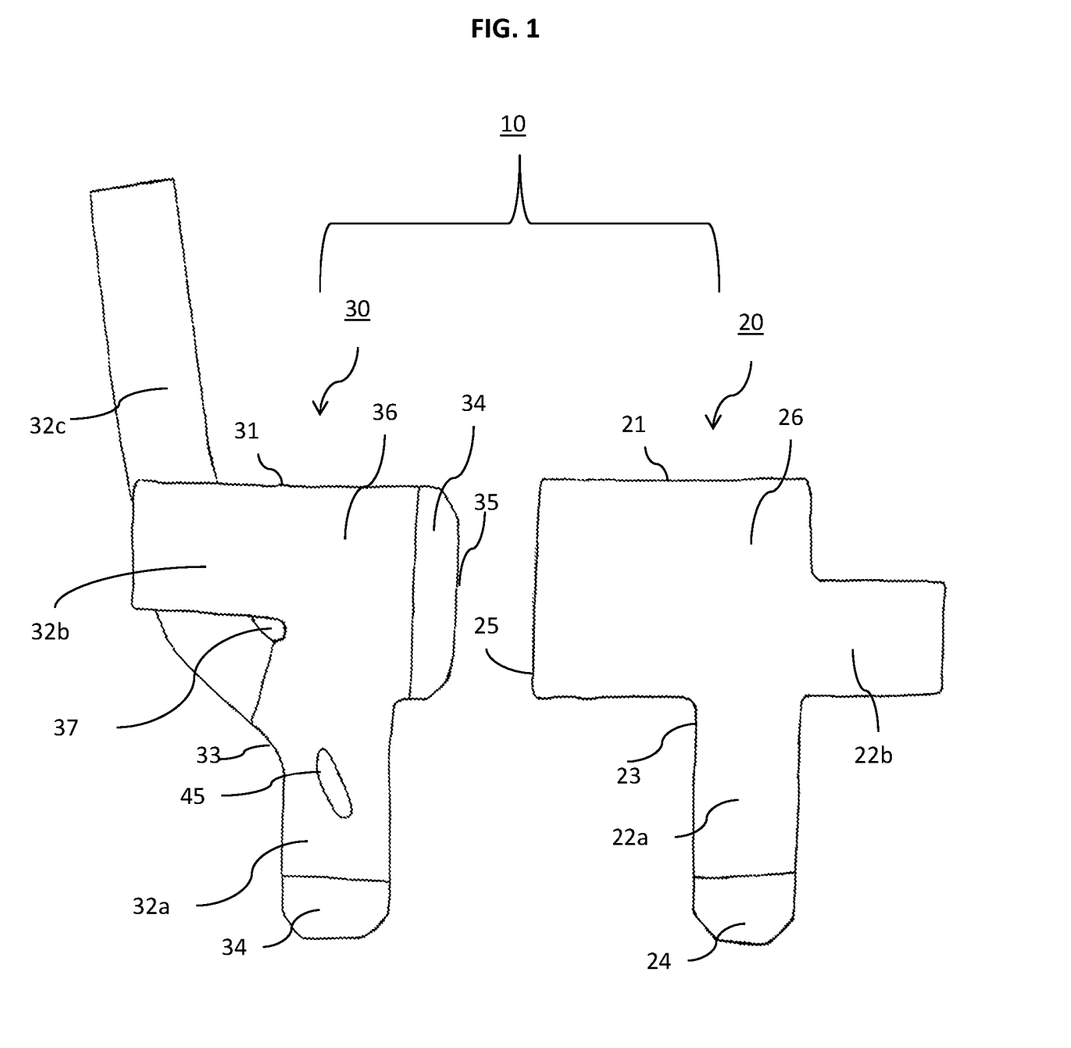
FIG. 1 depicts a top plan view of one exemplary embodiment of a compression garment of this disclosure in an unassembled state.

FIG. 1 depicts a top plan view of one exemplary embodiment of a compression garment 10 of this disclosure in an unassembled state, the garment being configured to wrap around a limb for compression therapy (e.g. a foot). The garment can include a body portion 20 and a spine portion 30. Each of portions 20, 30 can have a plurality of bands (e.g. bands 22 and/or bands 32 for adjusting tension of the garment 10). For example, as shown, body portion 30 can have a first band 32a, a second band 32b, and a third band 32c, though fewer bands 32 could be included or more than three bands 32 could be used as needed or required. The spine portion 20 can also be releasably attached onto the body portion 30 such that the spine portion 20 is positionable at different locations on the body portion 30, for example, to adjust a dimension of the garment such as the width. However, other dimensions of garment 10 could be adjusted by repositioning and/or reorienting spine portion 20 with respect to body portion 30.

Body portion 20 can include a central region 26 and/or one or more lateral regions. As shown, each of these regions can be formed from the same article or can be formed from separate articles or can be otherwise delineated with seams, dividers, or the like. Body portion 20 can include lateral side edges 25 that can be contoured with one or more curved edges, be a substantially straight edge, or some combination thereof. Spine portion 30 can also include a central region 36 and/or one or more lateral regions. Each of these regions can be formed from the same article or can be formed from separate articles or can be otherwise delineated with seams, dividers, or the like. Spine portion 30 can include lateral side edges 35 that can be contoured with one or more curved edges, be a substantially straight edge, or some combination thereof.

Bands 22, 32 of the body portion 20 and/or the spine portion 30 can be of a stiffer material than the corresponding regions 26, 36 (i.e. regions 26, 36 can be an elastic or less stiff material). The stiffer material can be capable of folding and conforming to contours of the limb thereby rendering the garment 10 less constricting when assembled on the limb. The materials of the body portion 20 and/or the spine portion 30 can also vary. For example, the body portion 20 can include an inner surface and an outer surface, the outer surface being stiffer or less flexible than the inner surface. Material properties between the body 20 and spine portions 30 can also vary. For example, the body portion 20 can be elastic or substantially elastic whereas the spine portion 20 can be inelastic or substantially inelastic.

At least one of the bands 32 of the spine portion 30 can be an ankle band. For example, band 32c can be an ankle band that is configured to extend away from an outer edge 33 opposite the inner edge 35 of the spine portion 30. Band 32c can be different than other bands 32 of the spine portion 30 (e.g., bands 32a and 32b in the depicted embodiment). For example, band 32c can be of a different shape, be longer, thinner, or constructed with different materials and/or different elasticity profiles than bands 32a, 32b of the spine portion 30. Band 32c can also be extended and curved from edge 33 curved away from the outer edge substantially normal to the upper edge of the spine portion. As can be seen, one band 32a can be extended from the outer edge 33 and substantially in parallel with edge 35. Band 32a can be oriented substantially normal to another band 32b extended from the upper edge 31 of the spine portion 30 and away from edge 35. Band 32c can be extended between bands 32a, 32b. A notch or indentation 37 for prevention of gapping can also be disposed between band 32c and band 32b and/or band 32a. However, spine portion 30 is not so limited and instead of a notch or indentation being formed on spine portion 30 itself, the bands 32a, 32b, 32c could have curved or indented surfaces to prevent gapping during assembly with the limb.

The body portion 20, spine portion 30, and/or corresponding bands 22, 32 can also include one or more compression portions. The one or more compression portions can be inelastic. For example, if the fluctuation range of garment 10 is desirous of being adjusted, one or more compression portions of inelastic material can be positioned on the outer surface of body portion 20 and/or spine portion 30 after garment 10 has been donned by the user. In turn, an elasticity profile of the garment 10 can be adjusted from a first elasticity profile to a second elasticity profile. As a result, the range of compression fluctuation the garment 10 applies to the limb during normal wear changes. The compression portion can also be an upraised portion selectively positioned and operable to apply pressure to an area of the user.

The distal end of one or more of the bands 22, 32 can include a detachable fastener tab 24, 34. The respective band 22, 32 of either portion 20, 30 can be trimmable and the respective fastener tab 24, 34 can be detachably positioned on the distal end. The bands 32 of the body portion 30 and/or bands 22 of the spine portion 20 can also be trimmable. For example, to adjust a respective band 22, 32 of either portion 20, 30, the respective band 22, 32 can be trimmed (e.g. length, width, or some other dimension) and then a fastener 24, 34 can be attached to a distal end of the respective band. The tension in respective band 22, 32 can be adjusted by to moving the distal end to a plurality of different positions to accommodate a plurality of different sized limbs and/or treatment profiles (e.g. different sized feet and/or different foot circumferences). While not depicted, the proximal end of each band 22, 32 can also be releasably attached to respective portion 20, 30.

Figure 2:
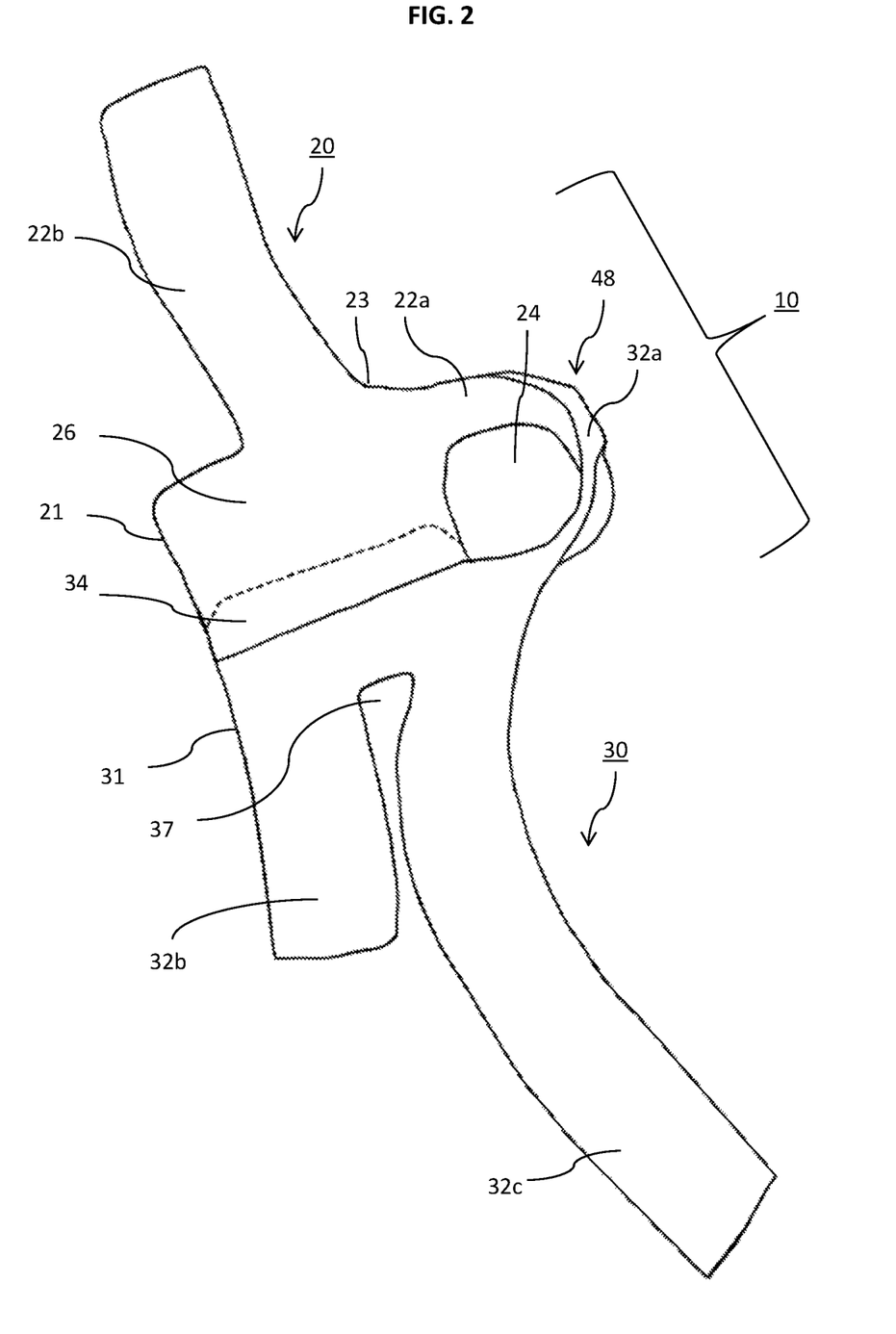
FIG. 2 depicts a top perspective view of the garment of FIG. 1 in an assembled state.

The spine portion 30 can include an aperture 45 in at least one of the bands (e.g. bad 32a as shown). A corresponding band 22a of body portion 20 in turn can extend from an edge (e.g. edge 23) of the body portion 20, including edge 33 and be caused to pass through the aperture 45 and interlock with corresponding band 32a. In some embodiments, passing through and interlocking the band 32a of the body portion 30 with the spine portion 20 can form a heel cup 48 as shown in FIG. 2 which shows a top perspective view of garment 10 in an assembled state. Cup 48 can be a contoured surface operable to conform to, receive, and/or support a heel. Cup 48 can also be operable to adjust a distal end of the garment to a plurality of different foot lengths and/or align an arch portion of garment 10 over the foot. For example, the cup 48 can be a chamber with an open upper end and curved, closed lower edge formed between interlocked bands 22a, 32a. Cup 48 may not necessarily be closed at the bottom but may still receive, support and otherwise conform to a heel when inserted therein.

Figure 3:
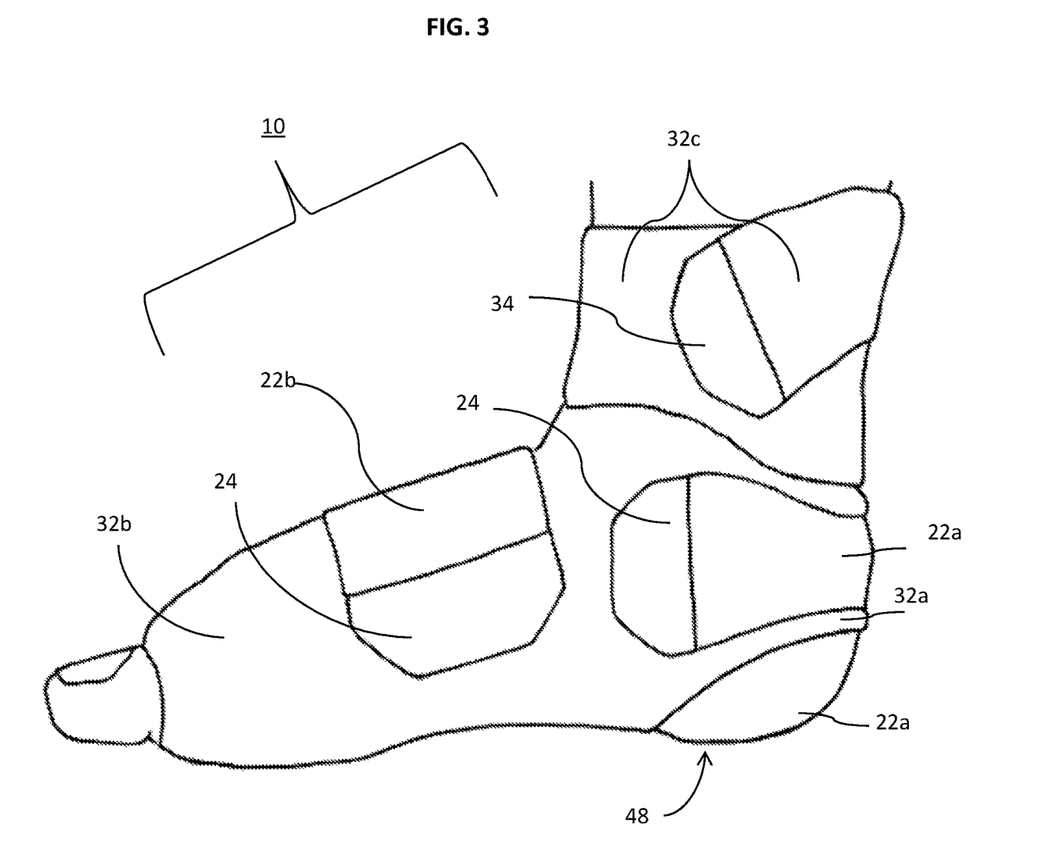
FIG. 3 depicts a side perspective view of an example garment of this disclosure during fitting and/or attachment to a patient.

The advantage and shape of cup 48 can be seen in FIG. 3, wherein a side perspective view of garment 10 is shown during fitting and/or attachment to a foot. As shown, band 32c can be wrapped around the ankle of the foot and be secured with fastener tab 34. The band 32c can be relatively long at the outset of use be capable of wrapping the ankle multiple times, or trimmed to a shorter length. In this regard, material properties of band 32c can differ from other bands 32a, 32b as needed or required.

Bands 22 of body portion 20 can also be adjusted relative to bands 32 of spine portion 30. For example, band 22b can be pulled in an opposing direction to band 32b around the foot. The bands 22, 32 can also be trimmed to the appropriate dimension length and then secured into its position and orientation. Advantageously, by adjusting the position of the spine portion 30 along the trimmable section of the body portion 20 (e.g. on or about edge 25 of body portion 20), the location of the interlocking bands 22a, 32a can be translated or moves up or down relative to the heel of the user.

Figure 4:
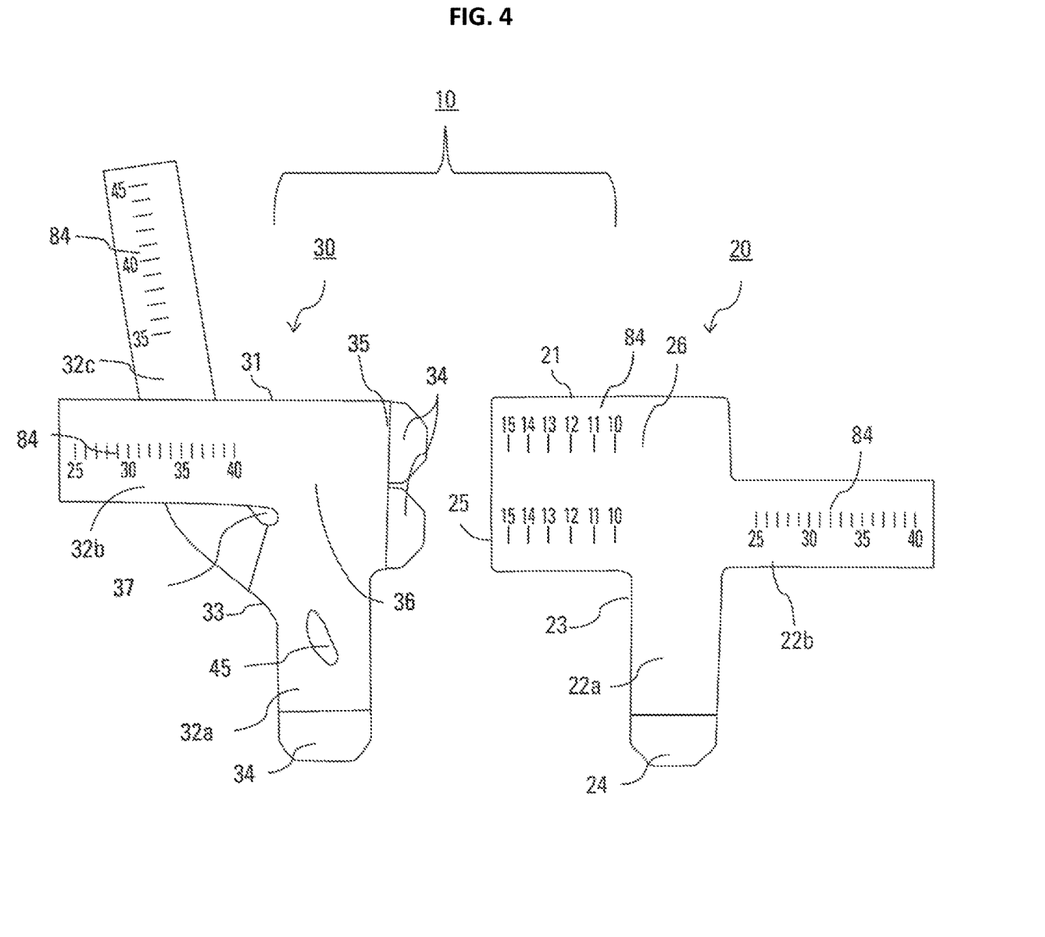
FIG. 4 depicts a top plan view of one exemplary embodiment of a compression garment of this disclosure in an unassembled state.

Turning back to FIG. 1, inner edge 35 of spine portion 30 can attach onto the body portion 20 in a plurality of different positions and/or orientations. The inner edge 35 can include one or more detachable fasteners 34. For example, while the embodiments of FIG. 1 show only one fastener 34 disposed on edge 35, the embodiment of FIG. 4 shows two separate fasteners 34 with a space or gap between each fastener 34. The spine portion 30 can be independently angleable on the body portion 20 at a plurality of orientations and positions based on edge 35 and/or any corresponding fasteners 34.

Any number of fasteners 34 with edge 35 can be used as needed or required. As also shown in FIG. 4, the spine portion 30 and/or the body portion 20 can include indicia 84 corresponding to a dimension of the limb (e.g. one or more dimensions of the foot). Indicia 84 can be on or in communication with any of bands 32, 22, or any other portion of either body portion 20 or spine portion 30. Indicia 84 can be used to facilitate accurate sizing, trimming, and/or placement of garment 10 with the limb. For example, the dimension of the limb can be one of a plurality of foot circumferences, feet lengths, feet widths, feet heights, ankle or any other dimension, such that the spine portion 30 can be trimmable along the indicia 84 to conform to the respective one or more dimensions of the user. The indicia 84 can also be used for arch circumferences or circumference in the metatarsal area.

Indicia 84 can be for shortening a dimension (e.g. a length) of the garment 10, whereby the indicia 84 as shown can be the smaller numbers imprinted on body portion 20 and the spine portion 30 that can be used to correspond to a dimension of the user. As can be seen, indicia 84 may be one or more alphanumeric characters (e.g. the relatively small numbers listed) positioned on body portion 20 and spine portion 30 by being printed, painted, glued, heat transferred, sewn onto or otherwise attached thereon. Indicia 84 could also be dots, geometric shapes, symbols, patterns, tick marks, text, or the like spaced at intervals therealong. The indicia 84 can be positioned in one or more regions 26, 36 of the body portion 20 and/or the spine portion 30.

For example, as shown, there may be indicia 84 on or adjacent the upper edge 21 of the body portion 20, on or adjacent the lower edge 23 of the body portion 20, in the central region 26, or anywhere else on the body portion 20 to be able to accurately and easily trim the body portion 20 to conform to the limb. Similarly, there may be indicia 84 on or adjacent the upper edge 31 of the spine portion 30, on or adjacent the lower edge 33 of the spine portion 30, in the central region 36, or anywhere else on the spine portion 30 to be able to accurately and easily trim the spine portion 30. In some embodiments, the body 20 and/or spine portion 30 can be trimmable between its edges so that either portion 20, 30 can correspond to any shape of the limb. Advantageously, as the user's respective dimension changes during or as a result of treatment (e.g. the ankle circumference changes as result of the foot or ankle being reshaped through compression therapy), the spine portion 30 and/or body portion 20 and any respective bands 22, 32 can be conformed to the user without the need to replace with a separate garment or any constituent component.

Figure 5:
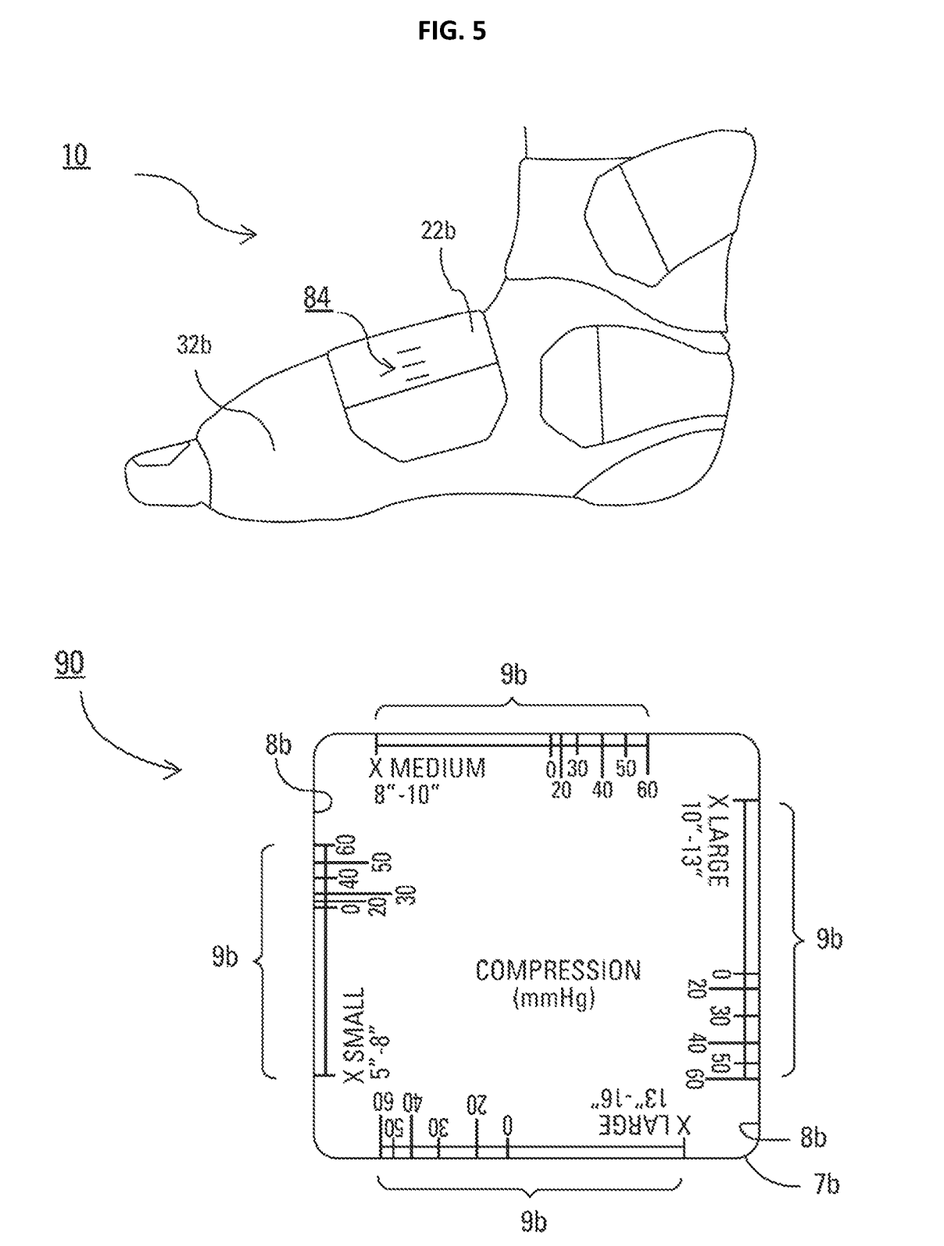
FIG. 5 depicts an embodiment of the garment with an exemplary compression measuring system that includes indicia on an exemplary band.

Turning to FIG. 5, an exemplary compression garment 10 including band 22b is shown with an exemplary compression measuring system. Each band 22b as previously described may be elastic or substantially elastic along its length or longitudinal axis (e.g. the axis along which tension is to be applied). Each band 22b may alternatively be elastic along only a part of its length. Each band 22b may have visual indicators such as indicia 84 printed along its elastic length, or elastic axis, spaced by intervals. Each interval may have a fixed or specified length when respective band 22b is not under tension. Each of bands 22b may be pulled under tension around the limb (e.g. foot as depicted) at a selected location, attached to itself and/or attachable to other portions of garment 10, using a fastener 24 and thus applying compression to that portion of the limb.

As can be seen, indicia 84 may include one or more tick marks spaced along band 22b at intervals. However, indicia 84 is not so limited and could include dots, geometric shapes, symbols, patterns, text, or the like spaced at intervals therealong for measurement with the referenced measuring device such as a calibrated scale or card upon donning of band 22b. Each interval may be spaced at a predetermined distance from each other when the bands 32 are unstretched. In contrast, when band 22b is under tension, the spacing between each indicia 84 may serve to accurately measure compression delivered by garment 10 to the foot at one or more multiple locations. For example, an interval between successive indicia 84 may increase when band 22b is under tension and lengthens. The distance between successive indicia 84 may then be measured after application of garment 10 to the foot, wherein the measured distance may indicate tension in band 22b and in turn the specific amount of compression applied by garment 10 to the foot.

Figure 6A:
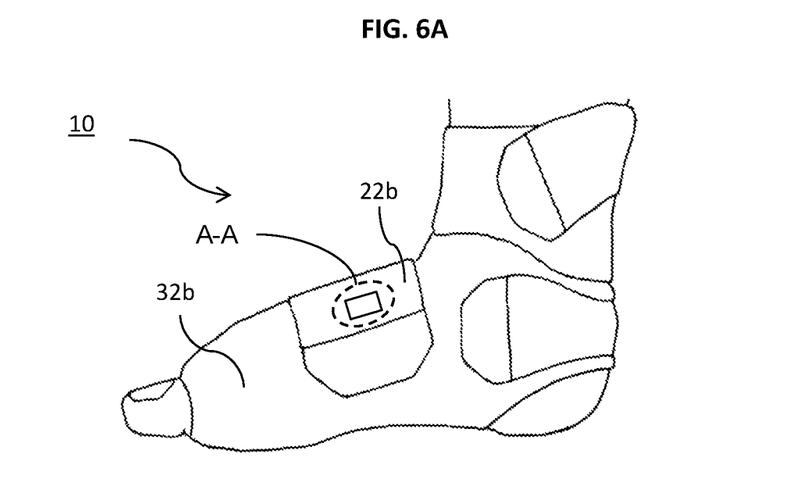
FIG. 6A depicts a close up view of an example band of the garment with an exemplary multi-layer compression measuring system.
Figure 6B:
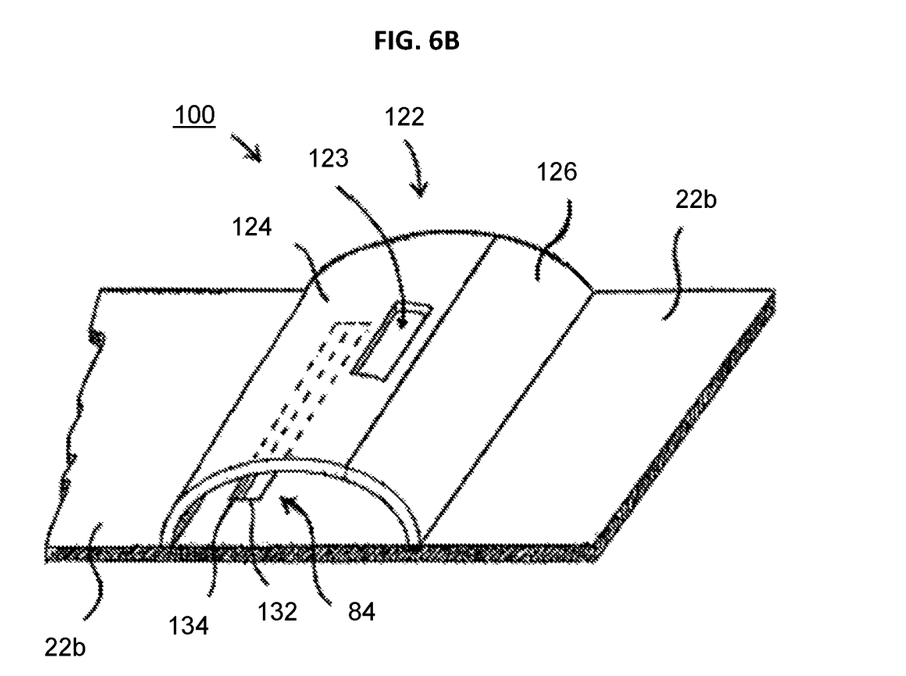
FIG. 6B depicts a close up view of plane A-A of FIG. 6A with an exemplary multi-layered compression measuring system in one of the bands prior to stretching.
Figure 8:
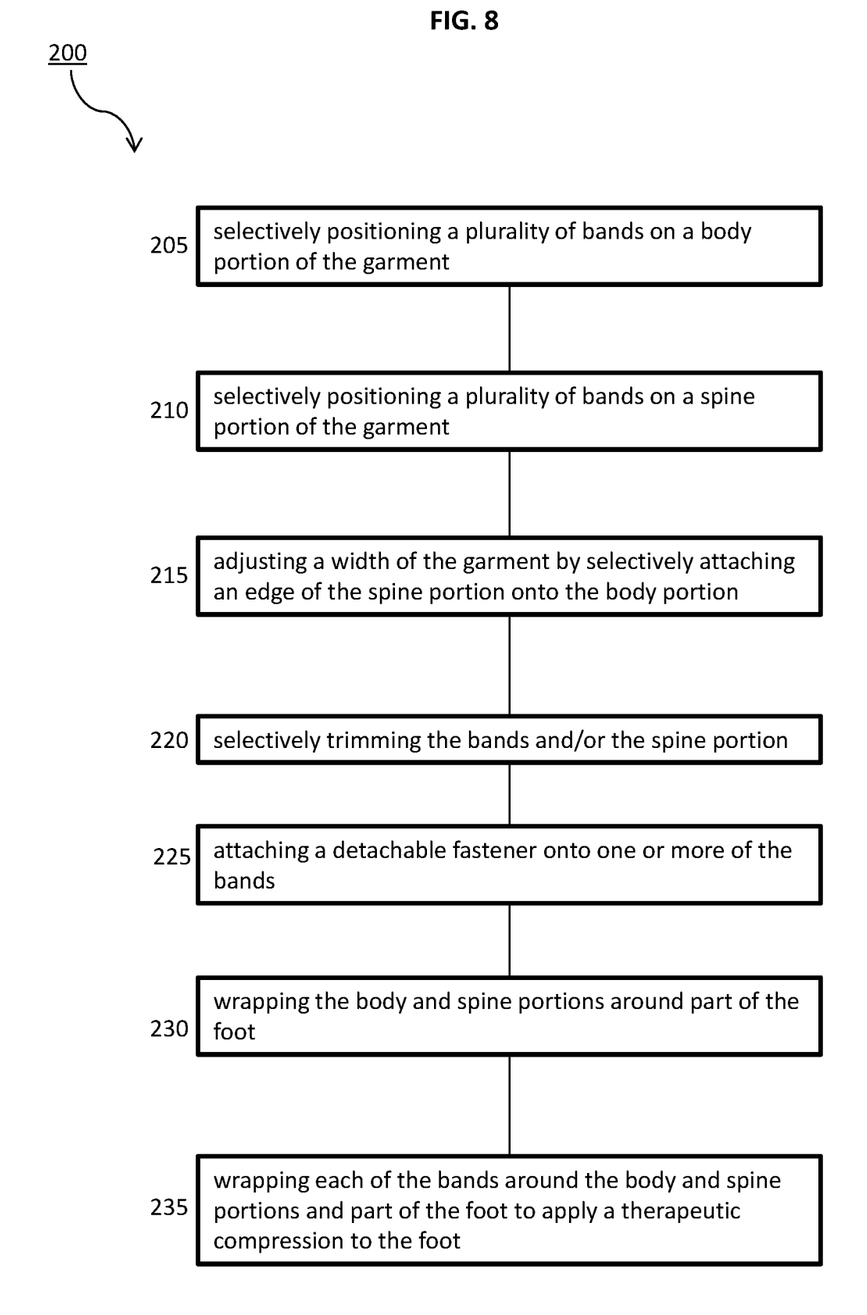
FIG. 8 depicts a schematic overview of a method of assembling an example garment of this disclosure.

Systems of measuring compression levels and/or tension associated with bands 32 and garment 10 are also contemplated such as using the card 90 shown in FIG. 8. Card 90 may be used to determine tension at multiple locations of band 22b as well as multiple locations about the limb when assembled with garment 10. After measuring, band 22b can optionally be removed, relocated, and/or adjusted by releasing fastener 24, selectively positioning said fastener 24, and re-fastening fastener 24 to the selected location, orientation, and/or desired tension. Card 90 may include reference numerals 7a-7c disposed adjacent a plurality of edges 8a-8c with measurement scales 9a-9c calibrated to measure the distance between indicia 84 in the band 22b. FIGS. 6A through 6B show certain non-limiting embodiments of a multi-layer compression measurement system 100 for use with one or more of bands (e.g. 22b, 22a, 32a, 32b, 32c) and/or any portion of body portion 20 and/or spine portion 30.

Figure 7A:
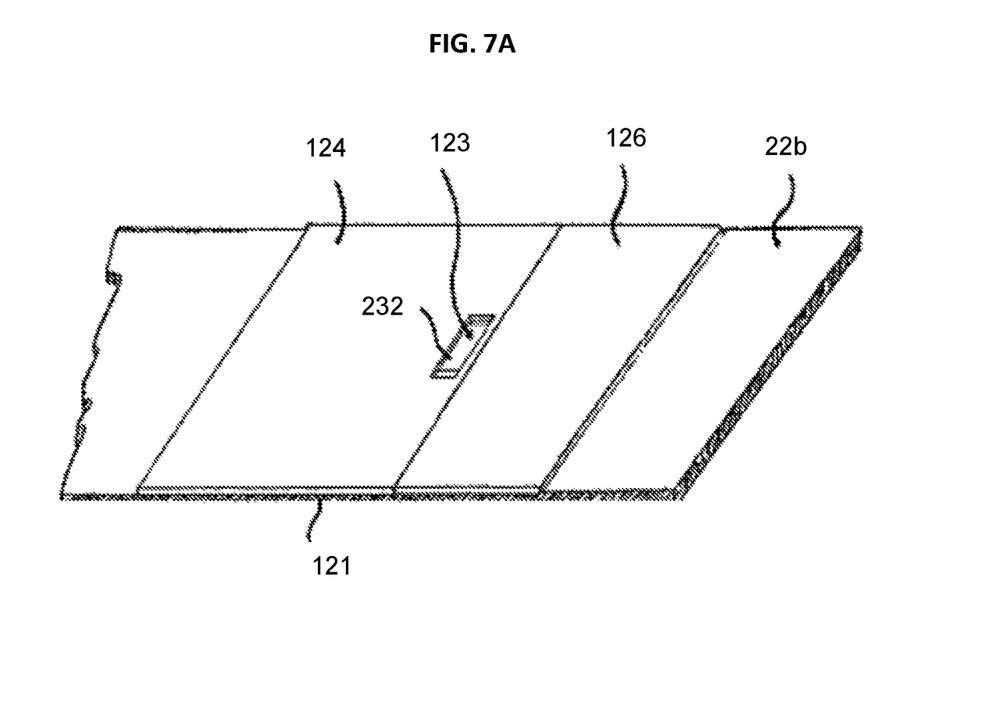
FIG. 7A is a perspective view of the measurement system of FIG. 6B with a predetermined tension applied to the band.
Figure 7B:
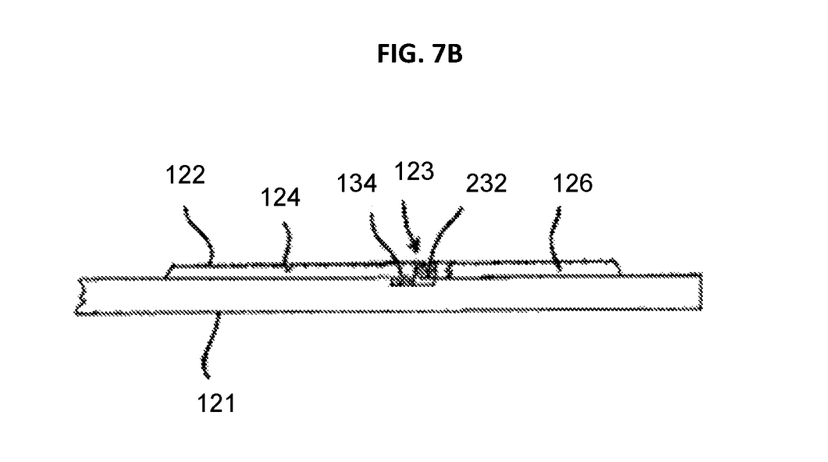
FIG. 7B is a sectional side elevation view corresponding to FIG. 7A.

System 100 can be installed in one or more of the bands of the garment 10 as shown in FIGS. 6A through 6B but can be incorporated in any portion of garment 10 including portions of portion 20. FIG. 6B is a perspective view of system 100 including a stretchable base layer 121 having indicia 84 thereon; and a stretchable upper layer 122 positioned on top of the stretchable base layer. Importantly, stretchable upper layer 122 comprises a first portion 124 and a second portion 126 joined end-to-end. Importantly as well, first portion 124 and second portion 126 can have different stiffnesses. For example, first portion 124 may be inelastic and second portion 126 may be elastic. One end of first portion 124 is attached (e.g.: sewn) to base layer 121 and one end of second portion 126 is also attached (e.g.: sewn) to base layer 121, as illustrated. The other ends of first and second portions 124 and 126 are also attached (e.g.: sewn) together, as also illustrated. FIG. 7A is a perspective view of the measurement system 100 of FIG. 6B with a predetermined tension applied to the band 32. FIG. 7B is a sectional side elevation view corresponding to FIG. 7A.

It is to be understood that either or both of the two layers in system 100 may in turn be made of two, three or more layers or sections connected together, and therefore any references in the specification and claims to two layers refer to at least two layers, each made of one, two, three or more layers or sections connected together. Additionally, indicia 84 may be positioned on system 100 by being printed, painted, glued, heat transferred, sewn onto or otherwise attached to the upper surface of base layer 121. In one preferred embodiment, indicia 84 comprise marking 132 and a red marking 134. In other embodiments, the indicia may comprise a tension force scale calibrated to display different tension levels. In operation, indicia 84 can be seen by a user through window 123 in first portion 124 of top layer 122. Other potential systems of measuring can include tension strain gauges, pressure sensors, and/or other bio-feedback sensors in one or more locations of the garment.

FIG. 8 depicts a schematic overview of a method 200 of assembling an example garment of this disclosure. The method can include 205 selectively positioning a plurality of bands on a body portion of the garment; 210 selectively positioning a plurality of bands on a spine portion of the garment; 215 adjusting a width of the garment by selectively attaching an edge of the spine portion onto the body portion; 220 selectively trimming the bands and/or the spine portion; 225 attaching a detachable fastener onto one or more of the bands; 230 wrapping the body and spine portions around part of the foot; and 235 wrapping each of the bands around the body and spine portions and part of the foot to apply a therapeutic compression to the foot. Other steps can be included as described throughout this disclosure.

From the perspective of the therapist or other professional facilitating donning, the herein disclosed garment advantageously allows the therapist to have one garment capable of fitting any patient without having to measure them to determine product size. This permits the therapist them to start treatment immediately, similar to bandaging. However, unlike bandaging, garments such as those embodiments herein with ankle foot wrap features simplify self-management thus allowing end-users to adjust the garment as swelling reduction is achieved. More importantly, this improves treatment results while also permitting the patient to easily remove and re-apply their garments which promotes better hygiene.

Other garments and compression stocking options are limited since they delay and reduce treatment time. Specifically, the patient needs to be measured prior to determining the product size, and then the patient is required to order or find a dealer location where they can purchase the product. This can take weeks which delays treatment and may lead to increased treatment expense for patients resulting in unnecessary therapy sessions for further fitting. Additionally, if the patient has significant edema reduction, the proposed solution can simply be resized so that further reduction can be achieved, where as other options require that a smaller size garment be ordered before treatment can continue.

The herein disclosed garment effectively contours the intricate shape of the human foot effectively enough to provide therapeutic compression. The herein disclosed garment overcomes those problems that have plagued the art, including trimming away an area(s) of excess material. In order for the garment to function as a form of compression therapy, the trimmed section can permit the wrap to more effectively contour the shape of the foot. The disclosed solution does just that by enabling the user to customize one or more body portions and/or bands of the wrap in accordance with the particular foot in order to further optimize the fit and therapeutic compression.

Other features and advantages of the disclosed solution will be apparent from the description herein. The examples are provided herein are solely to illustrate the invention by reference to specific embodiments. These exemplifications, while illustrating certain specific aspects of the invention, do not portray the limitations or circumscribe the scope of the disclosed invention. Many variations to those described above are possible.

What is claimed is:

1. A compression foot wrap garment for a foot, comprising:
a body comprising a central region with an inner edge, an outer edge opposite the inner edge, an upper edge, and a lower edge, and a plurality of bands forming the foot wrap garment, the plurality of bands of the body comprising at least one band extended from the outer edge and at least one band extended from the lower edge, wherein at least one band of the plurality of bands is longer than the other of the plurality of bands and is extended curved away from the outer edge substantially normal to the upper edge of the body;
wherein the foot wrap garment can accommodate different foot circumferences, widths, and lengths as a treatment of the foot progresses and changes the shape of the foot;
wherein the bands of the body are trimmable and comprise a detachable fastener causing the band to move to a plurality of different positions to adjust the garment to a plurality of different sized feet.

2. The garment according to claim 1, wherein the body comprises an aperture in at least one of the bands, wherein at least one of the bands of the body extends from a lower edge of the body and passes through and interlocks with the aperture.

3. The garment according to claim 1, wherein the body comprises indicia corresponding to a dimension of the foot.

4. The garment according to claim 3, wherein the dimension corresponds to a plurality of feet circumferences, and wherein the body is trimmable along the indicia to conform to a circumference of the user.

5. The garment according to claim 3, wherein the dimension corresponds to a plurality of feet widths, and wherein the body is trimmable along the indicia to conform to a foot width of the user.

6. The garment according to claim 3, wherein the dimension corresponds to a plurality of arch circumferences, and wherein the body is trimmable along the indicia to conform to an arch circumference of the user.

7. The garment according to claim 1, wherein distal ends of one or more of the bands comprises a detachable fastener tab, and wherein the one or more of the bands is trimmable with the fastener tab being detachably positioned on the distal end.

8. The garment according to claim 1, wherein at least one of the bands of the body is an ankle band that extends away from an outer edge opposite the inner edge.

9. The garment according to claim 8, wherein the at least one band of the body for the ankle is longer and thinner than other of the bands of the body.

10. The garment according to claim 1, wherein a notch or indentation for prevention of gapping is disposed between the at least one band extended curved away from the outer edge and the other bands of the body.

11. The garment according to claim 1, wherein at least one of the body and/or at least one of the plurality of bands further comprises one or more compression portions.

12. The garment according to claim 11, wherein the one or more compression portions is an upraised portion selectively positioned and operable to apply pressure to an area of the user.

13. The garment according to claim 1, wherein the body comprises a top edge, a bottom edge and a pair of opposite side edges, wherein the body is trimmable between the edges permitting the body to correspond to any shape of the foot.

14. The garment according to claim 1, wherein the bands of the body are of a stiffer material and the body is of an elastic material.

15. The garment according to claim 14, wherein the body includes an inner surface and an outer surface, the outer surface being of a different stiffness than the inner surface.

16. The garment according to claim 1, wherein all of the bands are of a different stiffness than the body.

17. The garment according to claim 1, wherein one or more of the bands of the body are trimmable and comprise indicia for trimming.

18. The garment according to claim 1, wherein the bands of the body are substantially elastic and the body is inelastic or include one or more inelastic portions.

19. The garment according to claim 1, further comprising a compression and/or tension level measuring system in the garment for indicating an actual compression level delivered to the foot by the garment.

20. The garment according to claim 19, wherein the system is operable to measure indicia on the garment when the garment is donned by the foot with a card comprising a scale for measuring a separation of at least one indicia to determine an actual compression level to the foot associated with the separation; and
wherein at least one end of the plurality of bands of the body is releasably attachable to a plurality of locations and orientations so that the plurality of bands is adjustable between a plurality of compression levels according to the actual compression level measured by the system.

21. The garment according to claim 19, wherein the system is disposed on the body, comprising: a stretchable base layer; and an upper layer attached at two spaced-apart locations on top of the stretchable base layer; wherein a visual indicator of the actual compression level is positioned with the upper or base layers and is observable when the upper layer is pulled taut.

* * * * *